US012624329B2

(12) United States Patent
Fukami et al.

(10) Patent No.: US 12,624,329 B2
(45) Date of Patent: May 12, 2026

(54) FERMENTATION TANK FOR THE MULTIPLICATION OF MICROORGANISMS

(71) Applicant: TOTAL BIOTECNOLOGIA INDUSTRIA E COMERCIO S.A., Curitiba (BR)

(72) Inventors: Josiane Fukami, Curitiba (BR); Douglas Fabiano Gomes, Curitiba (BR); Juliana Marcolino Gomes, Curitiba (BR); Jonas Hipolito, Curitiba (BR)

(73) Assignee: TOTAL BIOTECNOLOGIA INDUSTRIA E COMERCIO S.A. (BR)

( * ) Notice: Subject to any disclaimer, the term of this patent is extended or adjusted under 35 U.S.C. 154(b) by 740 days.

(21) Appl. No.: 17/959,997

(22) Filed: Oct. 4, 2022

(65) Prior Publication Data
US 2023/0107779 A1 Apr. 6, 2023

(30) Foreign Application Priority Data
Oct. 5, 2021 (BR) .......................... 102021019990-3

(51) Int. Cl.
*C12M 1/04* (2006.01)
*C12M 1/00* (2006.01)
*C12M 3/00* (2006.01)

(52) U.S. Cl.
CPC ............ *C12M 27/04* (2013.01); *C12M 23/24* (2013.01); *C12M 23/38* (2013.01); *C12M 23/54* (2013.01)

(58) Field of Classification Search
CPC ........ C02F 3/201; C12M 27/04; C12M 27/02; C12M 29/06
See application file for complete search history.

(56) References Cited

U.S. PATENT DOCUMENTS

| | | | | |
|---|---|---|---|---|
| 5,972,661 | A | * 10/1999 | Kubera | C12M 27/02 261/87 |
| 6,432,698 | B1 | * 8/2002 | Gaugler | C12M 23/28 435/296.1 |
| 2013/0189767 | A1 | * 7/2013 | Cheng | C12M 41/12 435/295.1 |
| 2018/0010082 | A1 | * 1/2018 | Jaques | B01F 27/86 |
| 2020/0102204 | A1 | * 4/2020 | Saukkonen | F16K 31/508 |

* cited by examiner

*Primary Examiner* — Jonathan M Hurst
(74) *Attorney, Agent, or Firm* — Orrick, Herrington & Sutcliffe, LLP

(57) ABSTRACT

There is described a fermentation tank for the multiplication of microorganisms, particularly a vertical fermentation tank comprising aeration and agitation elements with low cost and high efficiency. Particularly, a fermentation tank for the multiplication of microorganisms (100) comprising an external structure (10) of longitudinal axis (L) and an inner container (20) which receives a mixture to be fermented, the fermentation tank (100) comprising an aeration and agitation element (30) arranged in the inner container (20) collinear with the longitudinal axis (L), the aeration and agitation element (30) comprising internally a plurality of sets of fins (40), each set of fins (40) being arranged axially parallel to each other along the longitudinal axis (L) to provide aeration and agitation of the mixture to be fermented.

8 Claims, 8 Drawing Sheets

FERMENTATION TANK FOR THE MULTIPLICATION OF MICROORGANISMS

FIELD OF THE INVENTION

The present invention refers to a fermentation tank for the multiplication of microorganisms with biotechnological potential, particularly a vertical fermentation tank comprising aeration and mechanical agitation elements with low cost and high efficiency.

CROSS-REFERENCE

This application claims priority to Brazilian Patent Application No. BR102021019990-3, filed Oct. 5, 2021,which is incorporated herein by reference in its entirety.

BACKGROUND

The transformation of substrates in products by means of a fermentation process uses, generally, equipment known as bioreactors.

The bioreactors are vessels, such as tanks for example, which control the temperature, pressure, pH, and agitation, among other parameters, of the substrate and inoculum inserted therein during the fermentation process.

To this end, the bioreactors known to the prior art are provided with a container or tank which receives the substrates, inoculum feed ducts, mechanical agitation systems with paddles driven by electric motors, aeration equipment and instruments for controlling temperature, pressure, pH among other parameters.

For the adequate feeding of oxygen for the aeration of the mixture, these bioreactors require predefined piping at the place of installation thereof, both for transfer of the inoculum as for the injection of compressed air. Additionally, this type of equipment presents higher consumption of energy, steam, and gas for the operation thereof, as well as greater investment costs in the manufacture and installation.

This is because, the known bioreactors demand a complex steam boiler structure for the sterilization thereof, air compressors and units for generating steam and air, making the change of location of this equipment difficult in a factory, for example. Maintenance also becomes more time consuming, increasing the equipment downtime.

OBJECTIVES OF THE INVENTION

Thus, the present invention has as objective to provide a fermentation tank for the multiplication of microorganisms, particularly a portable and low-cost vertical fermentation tank, comprising highly efficient aeration and mechanical agitation elements and which do not demand the use of motors for their operation.

BRIEF DESCRIPTION OF THE INVENTION

The present invention has as object a fermentation tank for the multiplication of microorganisms, comprising an external structure of longitudinal axis and an inner container which receives a mixture to be fermented. The fermentation tank comprises an aeration and agitation element arranged collinear with the longitudinal axis, the aeration and agitation element comprising internally a plurality of sets of fins, each set of fins being arranged axially parallel to each other along the longitudinal axis to provide aeration and agitation of the mixture to be fermented.

DETAILED DESCRIPTION OF THE INVENTION

According to a preferred embodiment and as can be seen in FIGS. 1 to 9, the fermentation tank for the multiplication of microorganisms 100, object of this invention, comprises an external structure 10 of longitudinal axis L and an inner container 20 which receives a mixture to be fermented.

Figure 1:
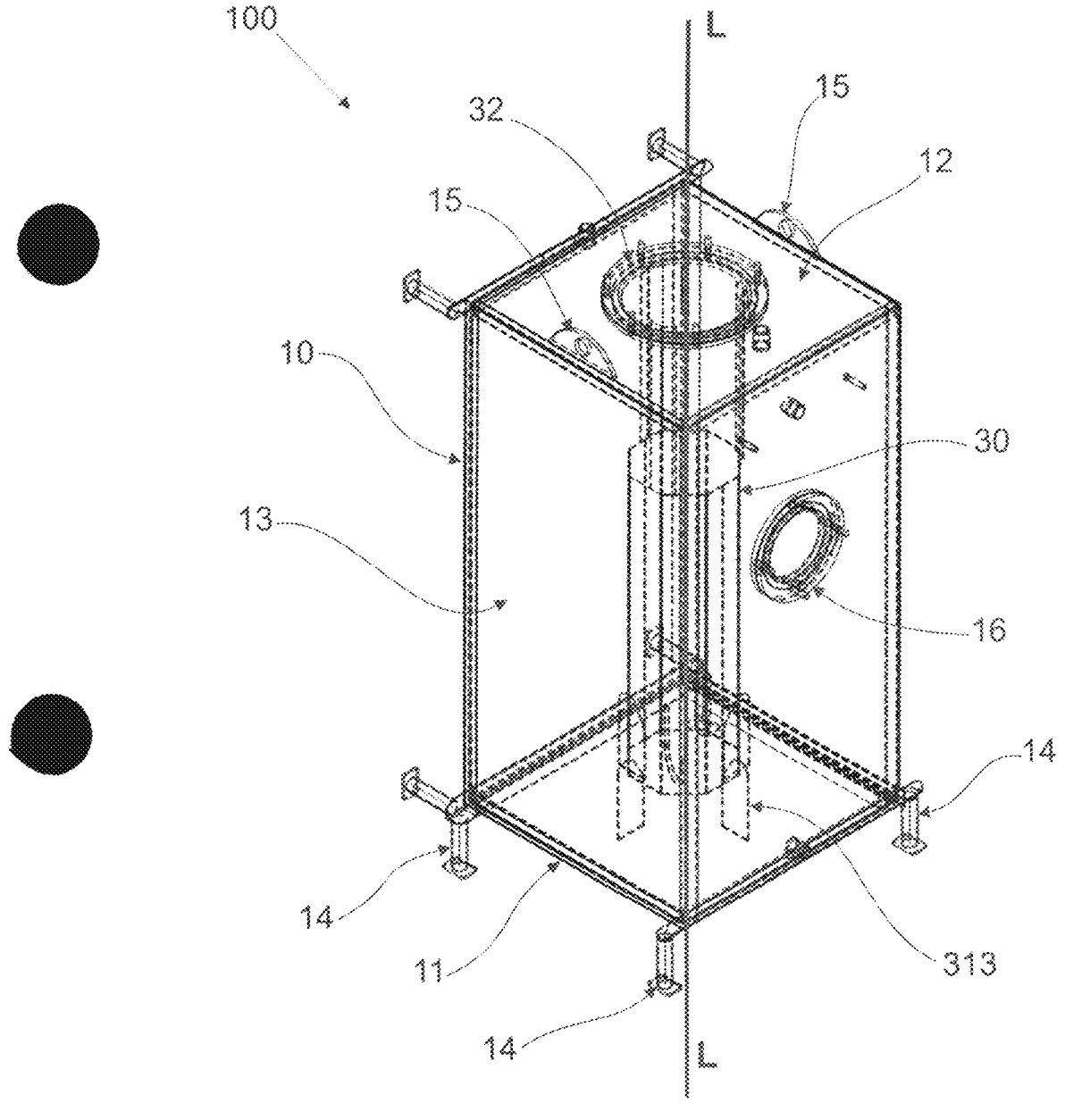
FIG. 1 is a perspective schematic view of the fermentation tank for the multiplication of microorganisms, object of this invention.
Figure 2:
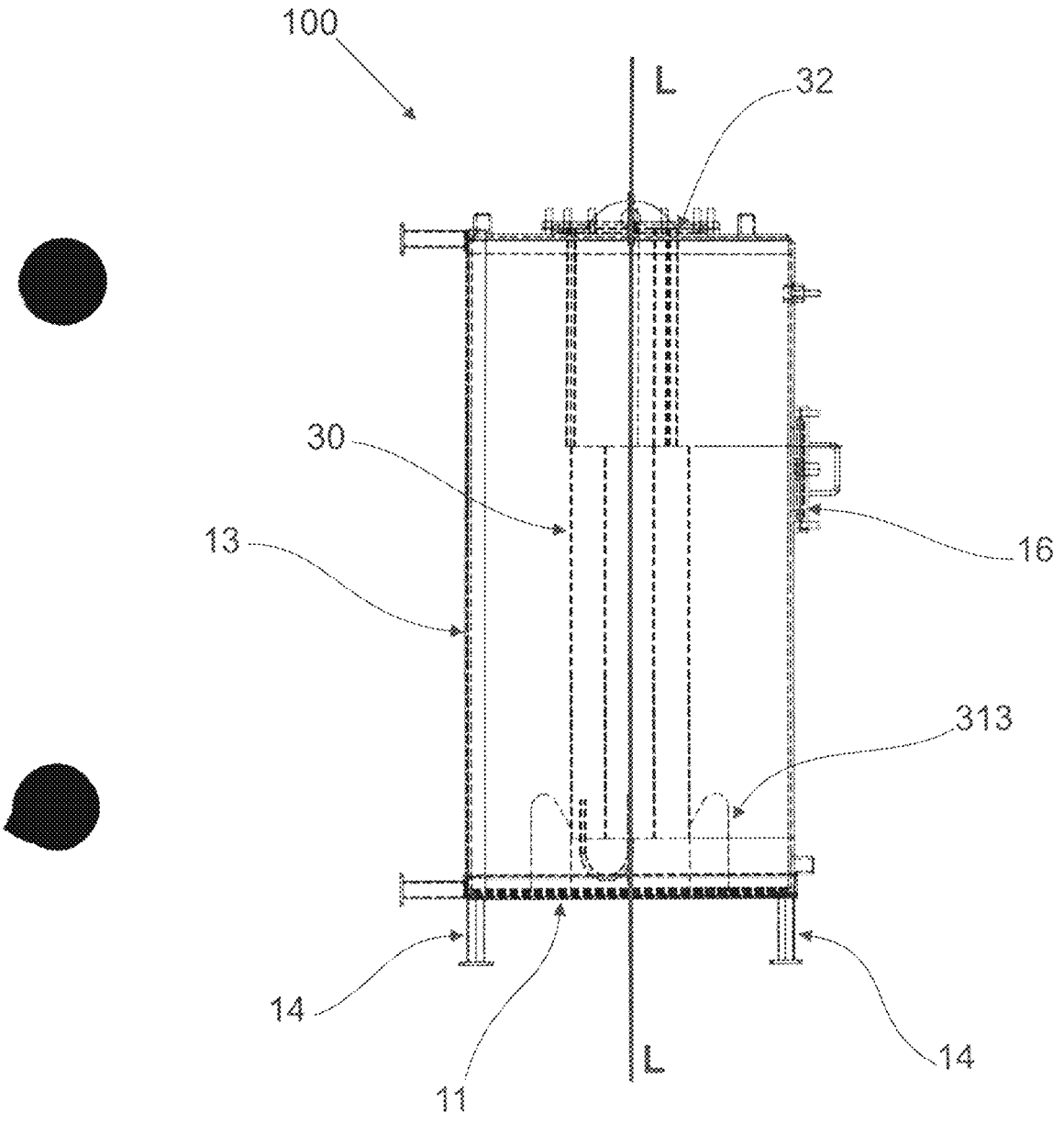
FIG. 2 is a lateral schematic view of the fermentation tank for the multiplication of microorganisms, object of this invention.

In this sense, as illustrated in FIGS. 1 and 2, the external structure 10 of longitudinal axis L of the fermentation tank 100 comprises a base 11, an upper portion 12 opposite the base 11 and side walls 13. The base 11 is comprised of support brackets 14 which maintain the fermentation tank 100 in the vertical position during the operation thereof, while the upper portion 12 is comprised of lifting handles 15 which help in the transport and displacement of the fermentation tank 100 in an easy and practical manner, by enabling the hitching of hoist chains to facilitate the change of position of the fermentation tank 100 or to allow the displacement thereof by means of a pallet truck, for example, or other suitable transport means.

At least one side wall 13 comprises an access inlet 16 to the inner container 20, that is, an opening for access to the mixture to be fermented which is arranged in the inner container 20 of the tank 100. This access inlet 16 includes a watertight cover and is used to facilitate the cleaning of the tank 100 and for the preparation of the culture medium or of the mixture.

Figure 3:
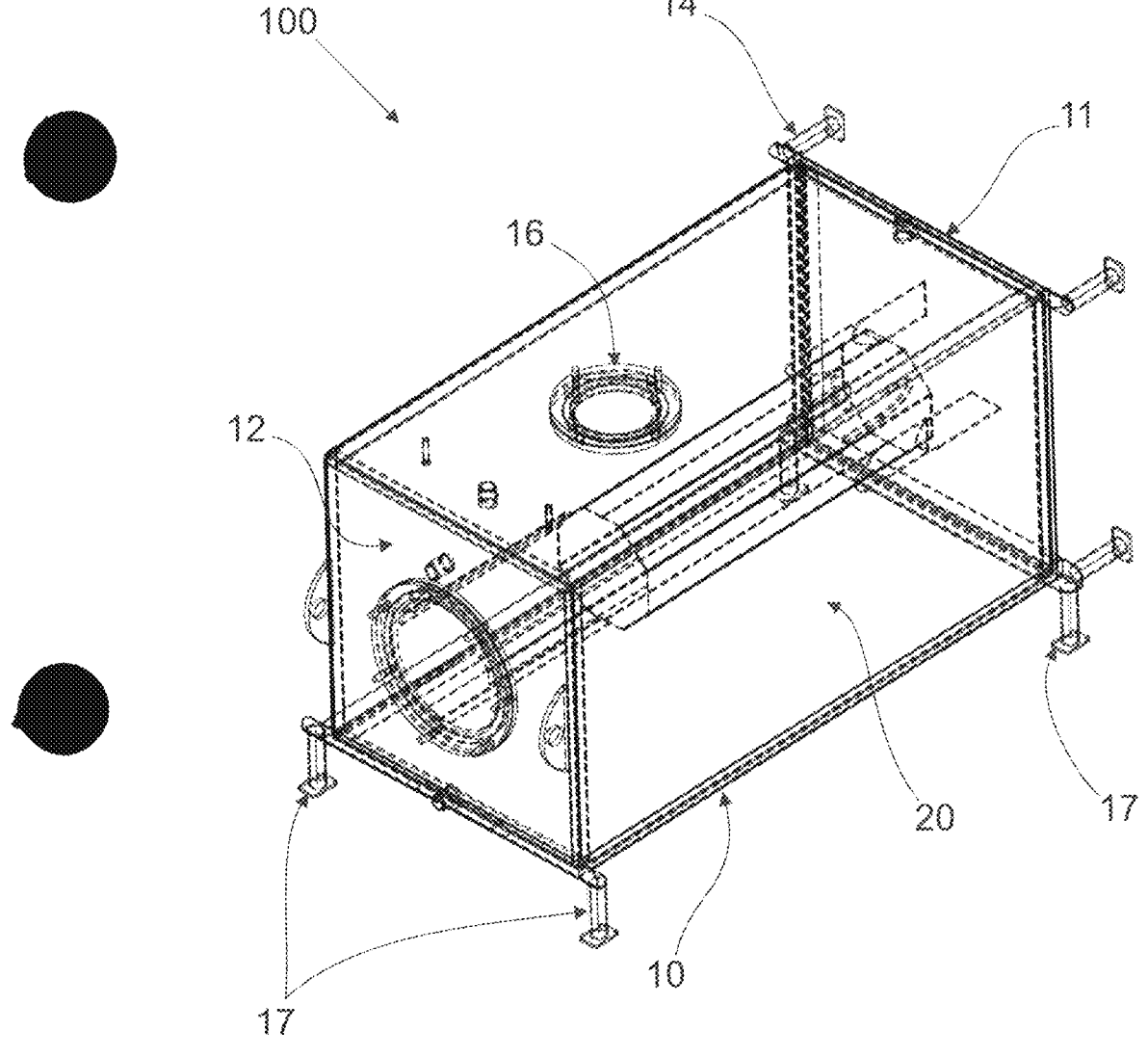
FIG. 3 is a perspective schematic view of the fermentation tank for the multiplication of microorganisms, object of this invention.

For the cleaning of the fermentation tank for the multiplication of microorganisms 100, the mixture is removed from the inner container 20 and the tank 100 is then sterilized in an autoclave. For the sterilization the tank 100 can be placed in the horizontal position as illustrated in FIG. 3. In this case, the tank 100 is supported on secondary brackets 17 which maintain it secure in the autoclave in the horizontal position.

The inner container 20 of the fermentation tank 100 comprises an aeration and agitation element 30, such as illustrated in FIGS. 4, 5, 6, 7A and 7B. This aeration and agitation element 30 is arranged in the inner container 20 collinear with the longitudinal axis L, as illustrated in FIGS. 1 and 2.

The aeration and agitation element 30 comprises a body structure 31 which receives internally the plurality of sets of fins 40 and an air inlet system 33. More specifically, the body structure 31 has an upper end 312 axially fixed to a cover 32 through which passes the air inlet system 33 to be connected to piping 34 which is radially arranged in the body structure 31.

Figure 4:
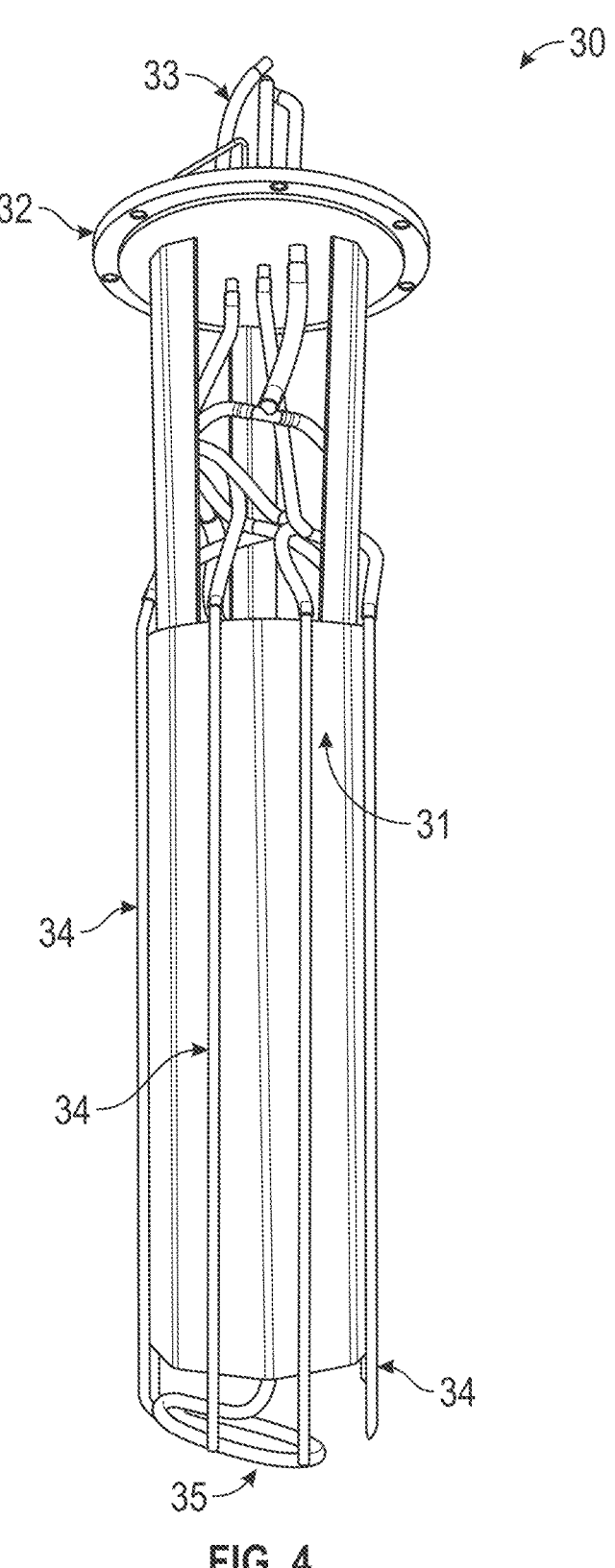
FIG. 4 is a picture illustrating the aeration and agitation element which comprises the fermentation tank for the multiplication of the microorganisms, object of this invention.
Figure 5:
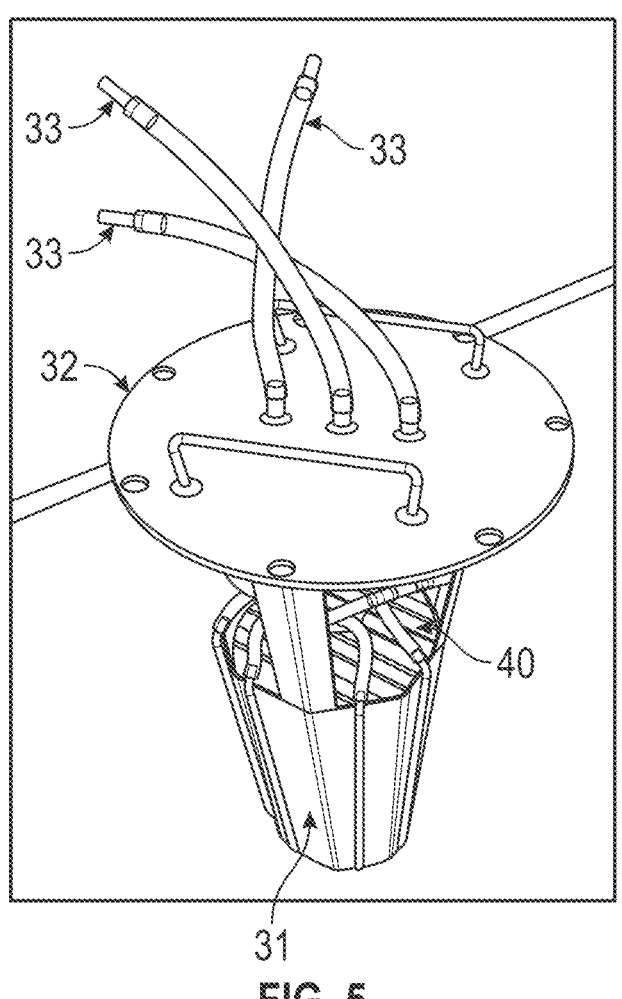
FIG. 5 is a picture illustrating an upper detail of the aeration and agitation element which comprises the fermentation tank for the multiplication of the microorganisms, object of this invention.
Figure 6:
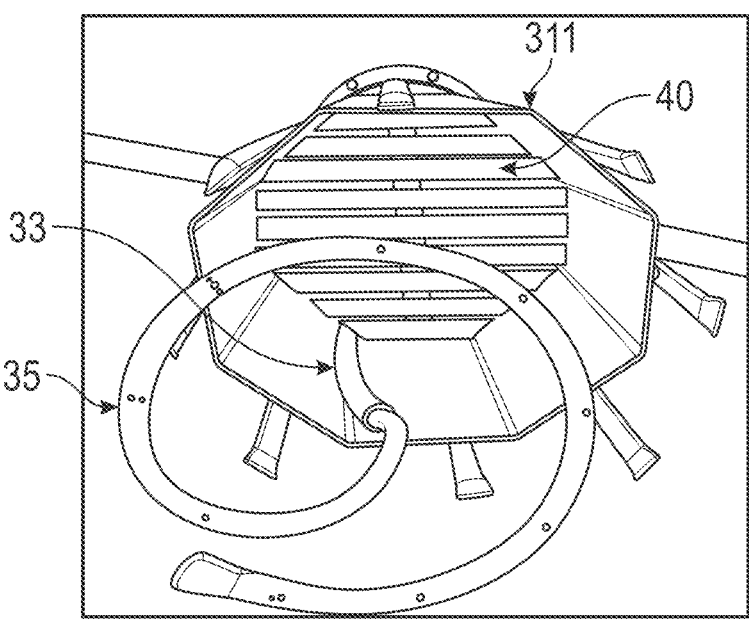
FIG. 6 is a picture illustrating an inner detail of the aeration and agitation element which comprises the fermentation tank for the multiplication of the microorganisms, object of this invention.
Figures 7A, 7B:
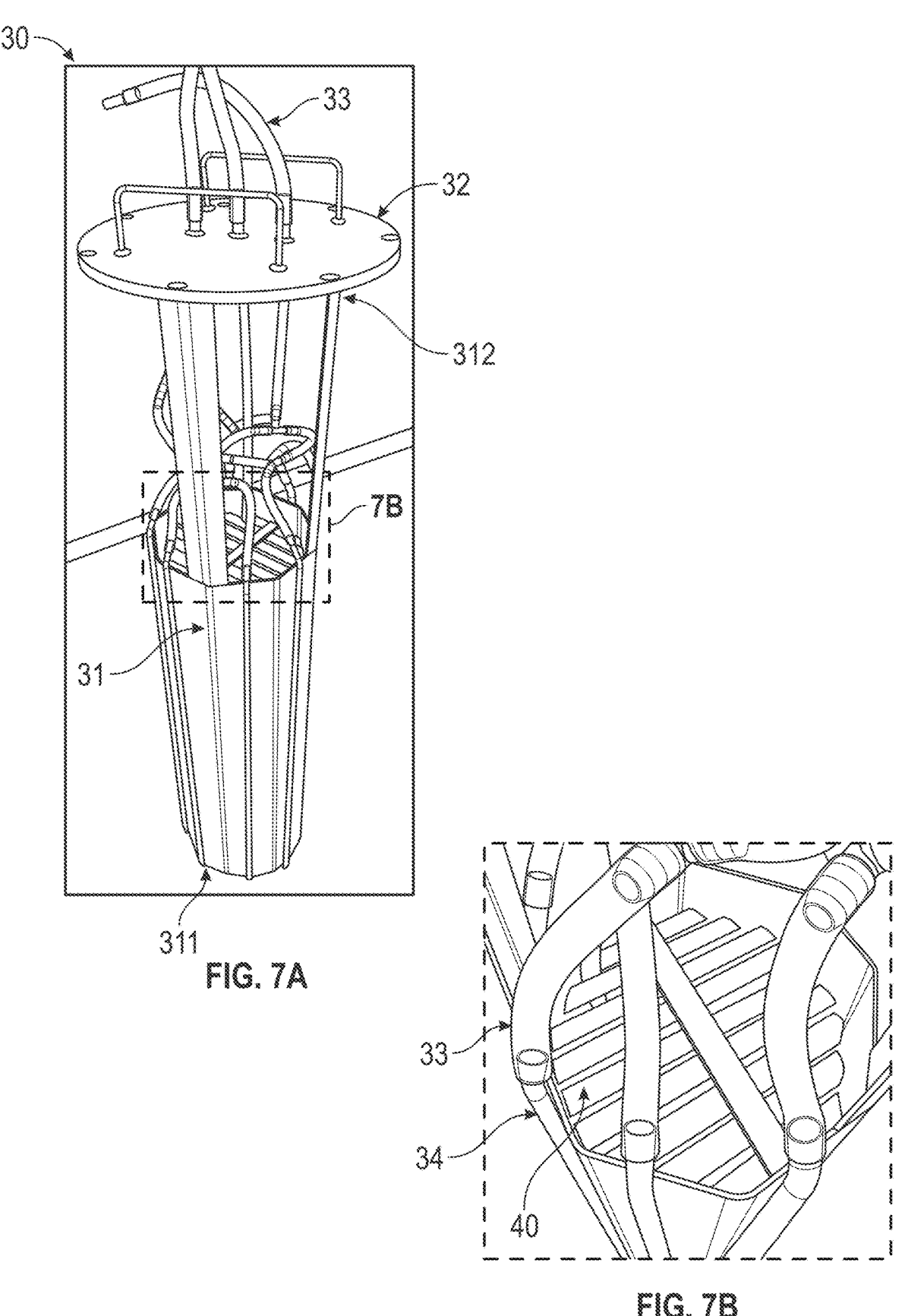
FIGS. 7A and 7B are pictures illustrating the aeration and agitation element and the detail of the set of fins arranged internally to the aeration and agitation element.
Figure 8:
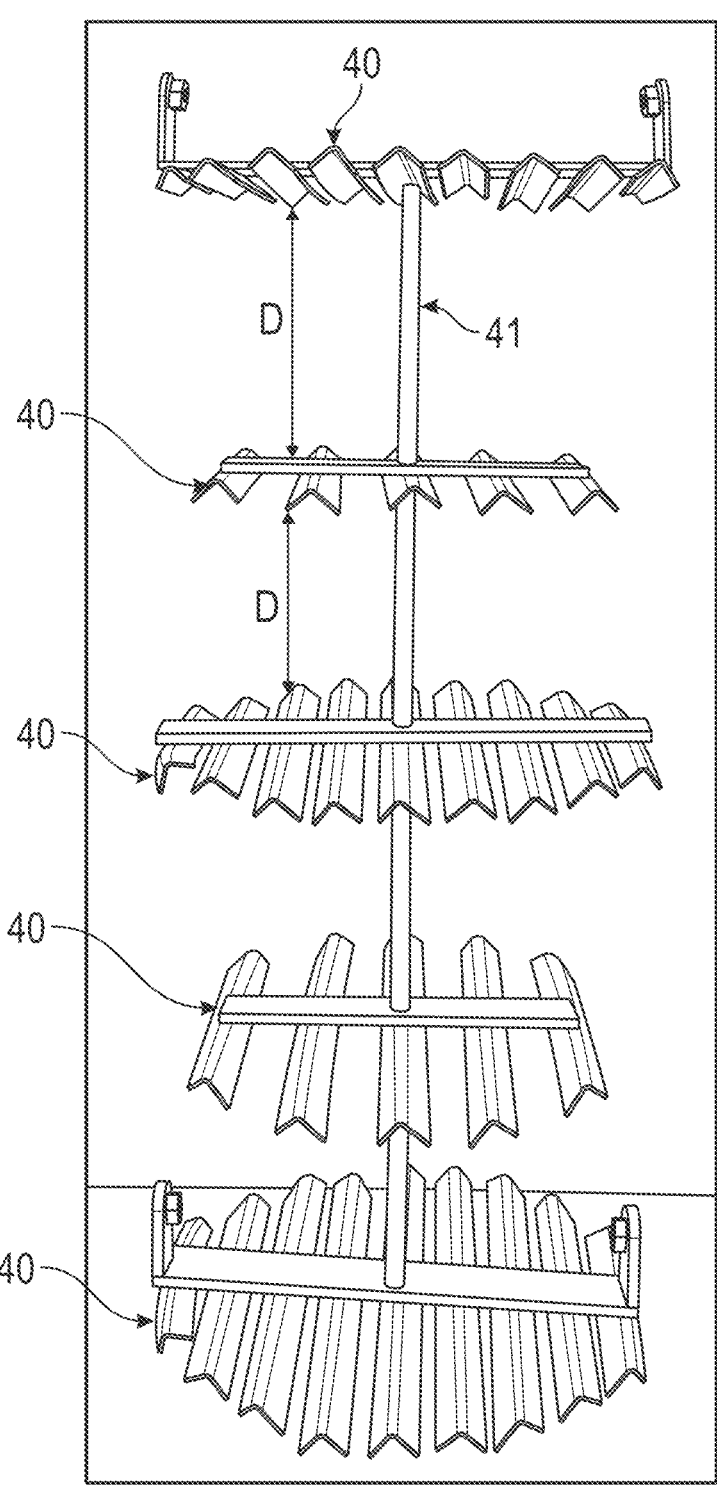
FIG. 8 is a picture illustrating the set of fins illustrated in detail in FIG. 7B.

The air inlet system 33, as illustrated in the pictures of FIGS. 4 and 5, is formed by a plurality of silicon ducts or hoses which receive the compressed air. Several silicon hoses of the air inlet system 33 are connected to the piping 34 of the body structure 31 which comprises from 3 to 10 holes of 1 mm along the length thereof, for the exit of air in the perpendicular direction to the longitudinal axis L of the fermentation tank for the multiplication of microorganisms 100. Further, the air inlet system 33, by means of a flexible silicon hose, is also directly pneumatically connected to a diffuser element 35 which is arranged at a lower end 311 of the body structure 31, opposite the cover 32. This diffuser element 35 consists in a spiral flexible piping, also comprising multiple air outlet holes with, preferably, equidistant holes and with 1 mm diameter each and which release the air in the vertical direction of the fermentation tank for the multiplication of organisms 100. In this way, there is promoted, in an efficient manner, the aeration of the system and homogenization of the components of the culture medium and microorganisms, overcoming, in a surprising manner, the absence of a mechanical agitation system present in conventional bioreactors.

Still in connection with the aeration and agitation element 30, this comprises internally to the structure of the body 31 a plurality of sets of fins 40, each set of fins 40 being arranged axially parallel to each other along the longitudinal axis L. As can be seen from the picture in FIG. 8, the plurality of sets of fins 40 is axially fixed along a connecting axis 41, so that each set of fins 40 is arranged axially parallel to each other at a variable distance D. The number of sets of fins 40 arranged in the aeration and agitation element 30 varies according to the volumetric capacity of the fermentation tank 100.

For the operation of the fermentation tank 100, the aeration and agitation element 30 is arranged in the inner container 20, collinear with the longitudinal axis L, so that the lower end 311 of the body structure 31 of the aeration and agitation element 30 is fixed internally to the base 11, by means of fasteners 313 and the cover 32 is positioned and fixed to the external structure of the upper portion 12 (FIGS. 1 and 2). In this way, the aeration and agitation element 30 is fixed inside the tank 100 by its ends, coincident with the longitudinal axis of the tank 100 and in the vertical position.

At this fixation position of the aeration and agitation element 30 in the inner container 20, the diffuser element 35 is positioned inside the tank 100 and parallel to the base 11, that is, at the bottom of the fermentation tank 100.

Figure 9:
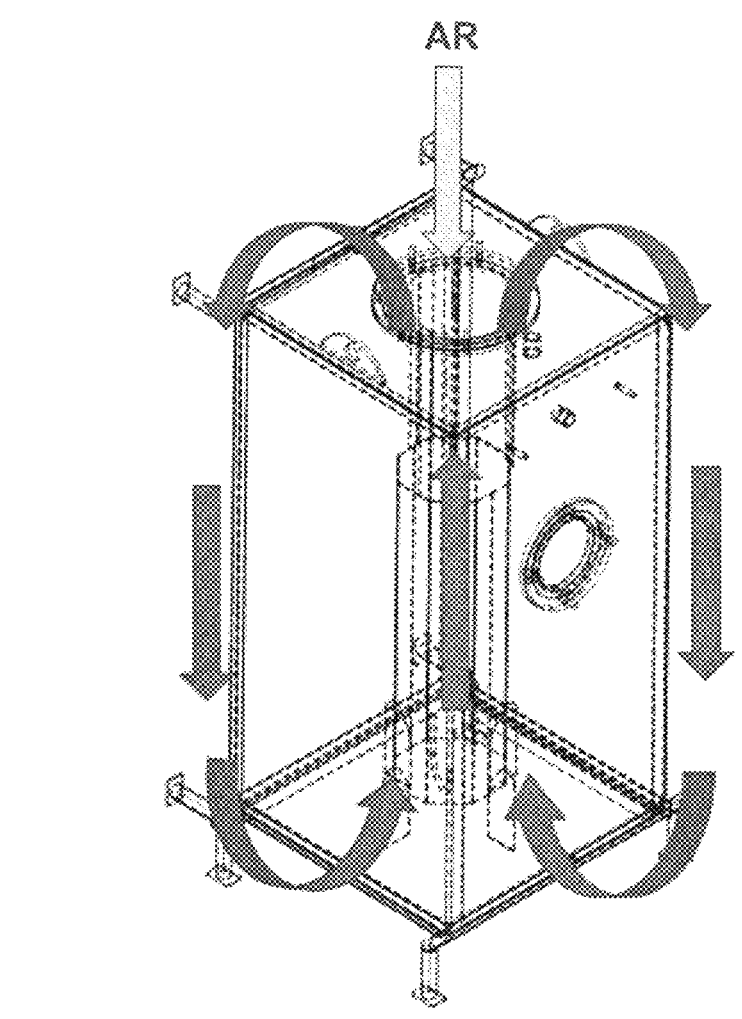
FIG. 9 is a schematic view of the aeration and agitation carried out in the fermentation tank for the multiplication of microorganisms, object of this invention.

Thus, as schematically illustrated in FIG. 9, the air inlet system 33 is connected to a compressed air line originating from a compressor or blower, providing the oxygen which passes through the air inlet system 33 of the aeration and agitation element 30 and through the piping 34 of the body structure 31, reaching the diffuser element 35. Therefore, the air is released by the holes of the piping 34 and by the holes of the diffuser 35 at the bottom of the tank 100, that is, in the mixture which is next to the base 11.

The air bubbles released by the piping 34 and by the diffuser element 35 in the lower part of the fermentation tank 100 rise, as indicated by the darker arrows in FIG. 9, inside the aeration and agitation element 30. Upon passing through the sets of fins 40 arranged inside the aeration and agitation element 30, the size of the air bubbles is reduced because the fins "break" the bubbles and, in this way, reduce the size of the oxygen bubbles, increasing the surface area for gas exchange inside the fermentation tank 100, as well as providing agitation of the mixture placed in the inner container 20, without the need for an agitation motor and other aeration equipment.

Thus, the aeration and agitation element 30 with the sets of fins 40 provides the oxygen for the fermentation and helps in homogenizing the mixture or broth placed in the inner container 20, that is, they provide the aeration and agitation of the mixture. As a result, there is an increase in the availability of oxygen, improving the fermentation.

Other advantages reached with the fermentation tank 100, object of this invention, are the low consumption of energy for the operation, since it is not necessary to use motors, there only occurs the feeding originating from the compressor or blower; low investment for the acquisition of equipment due to the simplicity of the components thereof and operation and little need of maintenance which results in less downtime of the equipment.

The low complexity of the fermentation tank 100 enables that it be sterilized in an electric autoclave, thus avoiding the demand for a steam boiler for the sterilization. Still in connection with the sterilization, this can be carried out with the tank 100 in the vertical or horizontal position, allowing a better flexibility of the size of the autoclave.

Additionally, since the fermentation tanks 100 can be easily displaced by pallet trucks, they provide flexibility to the operation.

Finally, the greatest advantage obtained with the fermentation tank 100 lies in its excellent performance in the multiplication and sporulation of microorganism, whether they are bacteria or fungi, due to the better homogenization and aeration of the mixture.

Having been described an example of a preferred embodiment, it must be understood that the scope of the present object covers other possible variations, being solely limited by the content of the attached claims, including therein the possible equivalents.

The invention claimed is:

1. A fermentation tank for the multiplication of microorganisms, comprising an external structure of longitudinal axis and an inner container which receives a mixture to be fermented, wherein the fermentation tank comprises an aeration and agitation element arranged in the inner container collinear with the longitudinal axis, wherein the aeration and agitation element comprises a body structure comprising internally a plurality of sets of fins and an air inlet system formed by a plurality of air ducts pneumatically connected to a diffuser element, wherein each set of fins is arranged axially parallel to each other along the longitudinal axis to provide aeration of the mixture to be fermented, and wherein the diffuser element consists of a spiral flexible piping comprising multiple air outlet holes that release the air in a vertical direction of the fermentation tank for agitation and homogenization of the mixture to be fermented.

2. The fermentation tank according to claim 1, wherein the body structure has an upper end axially fixed to a cover through which the air inlet system passes to be connected to the spiral flexible piping radially arranged in the body structure providing the connection of the air inlet system with the diffuser element, arranged at a lower end of the body structure, opposite to the cover.

3. The fermentation tank according to claim 2, wherein the diffuser element consists of a spiral piping equipped with multiple equidistant air outlet holes.

4. The fermentation tank according to claim 2, wherein the external structure comprises a base, an upper portion and side walls, the base having support brackets, the upper portion being comprised of lifting handles and at least one side wall comprising an access inlet to the inner container.

5. The fermentation tank according to claim 4, wherein the aeration and agitation element is arranged in the inner container collinear with the longitudinal axis so that the lower end of the body structure is internally fixed to the base of the external structure by means of fasteners and the cover is positioned and fixed to the external surface of the upper portion.

6. The fermentation tank according to claim 5, wherein the diffuser element of the aeration and agitation element is arranged in the inner container and parallel to the base.

7. The fermentation tank according to claim 1, wherein the plurality of sets of fins is axially fixed along a connecting axis, each set of fins being arranged axially parallel to each other at a variable distance.

8. The fermentation tank according to any one of the preceding claims, wherein the air inlet system is connected to a compressed air line.

\* \* \* \* \*